(12) United States Patent
Chen et al.

(10) Patent No.: US 12,220,436 B2
(45) Date of Patent: Feb. 11, 2025

(54) PROBIOTIC COMPOSITIONS AND USES THEREOF

(71) Applicant: National Taiwan University, Taipei (TW)

(72) Inventors: Ming-Ju Chen, Taipei (TW); Hsiao-Wen Huang, Taipei (TW)

(73) Assignee: National Taiwan University, Taipei (TW)

( * ) Notice: Subject to any disclaimer, the term of this patent is extended or adjusted under 35 U.S.C. 154(b) by 0 days.

(21) Appl. No.: 18/502,098

(22) Filed: Nov. 6, 2023

(65) Prior Publication Data

US 2024/0058400 A1 Feb. 22, 2024

Related U.S. Application Data

(62) Division of application No. 17/592,510, filed on Feb. 4, 2022, now abandoned.

(30) Foreign Application Priority Data

Feb. 5, 2021 (TW) .................. 110104506

(51) Int. Cl.
| | |
|---|---|
| *A61K 35/747* | (2015.01) |
| *A23L 33/135* | (2016.01) |
| *A61P 13/12* | (2006.01) |
| *C12N 1/20* | (2006.01) |
| *C12R 1/225* | (2006.01) |
| *C12R 1/25* | (2006.01) |

(52) U.S. Cl.
CPC .......... *A61K 35/747* (2013.01); *A23L 33/135* (2016.08); *A61P 13/12* (2018.01); *C12N 1/20* (2013.01); *C12N 1/205* (2021.05); *C12R 2001/225* (2021.05); *C12R 2001/25* (2021.05)

(58) Field of Classification Search
CPC ...... A61K 35/747; A23L 33/135; A61P 13/12
See application file for complete search history.

(56) References Cited

FOREIGN PATENT DOCUMENTS

AU 2015100952 A4 * 8/2015

* cited by examiner

*Primary Examiner* — Louise W Humphrey
*Assistant Examiner* — Alexander M Duryee
(74) *Attorney, Agent, or Firm* — Hannah Tien

(57) ABSTRACT

An isolated bacterial strain of *Lactiplantibacillus plantarum* subsp. *plantarum* MFM 30-3 deposited under the DSMZ Accession No. DSM 34213 is provided; a probiotic composition including an *Lactiplantibacillus plantarum* subsp. *plantarum* MFM 30-3 and optionally, one or more additional probiotic organisms that enhance the probiotic activity of the *Lactiplantibacillus plantarum* subsp. *plantarum* MFM 30-3 is also provided; and a method for preventing or treating chronic kidney disease in a subject in need thereof including: administering to the subject a pharmaceutically effective amount of the probiotic composition including an isolated bacterial strain of *Lactiplantibacillus plantarum* subsp. *plantarum* MFM 30-3, and optionally, one or more additional probiotic organisms that enhance the probiotic activity of the *Lactiplantibacillus plantarum* subsp. *plantarum* MFM 30-3 is further provided.

4 Claims, 14 Drawing Sheets

Specification includes a Sequence Listing.

(A)

(B)

PROBIOTIC COMPOSITIONS AND USES THEREOF

The present application is a Divisional Application of patent application Ser. No. 17/592,510, filed on Feb. 4, 2022, claiming priority to TW application No. 110104506, filed Feb. 5, 2021, which are incorporated herein by reference in their entireties.

This application also contains a Sequence Listing in a computer readable form, the file name is 4223-NTU-SEQ-Listing, created on Oct. 19, 2023, the size is 4000 bytes, which is incorporated herein by reference.

FIELD OF THE INVENTION

The present invention relates to a composition comprising *Lactiplantibacillus plantarum* subsp. *plantarum* MFM 30-3 (deposited the DSMZ Accession No. DSM 34213, either alone or in combination with one or more probiotic organisms, or an agent that may enhance the probiotic activity of *Lactiplantibacillus plantarum* subsp. *plantarum* MFM 30-3. Further, the present invention provides administration of *Lactiplantibacillus plantarum* subsp. *plantarum* MFM 30-3 in the probiotic composition to a subject in need for preventing or treating chronic kidney disease.

BACKGROUND OF THE INVENTION

Chronic kidney disease (CKD) is characterized by a substantial loss of kidney function and is emerging as a major risk factor for cardiovascular diseases. Thus, CKD is becoming a severe public health issue that desperately requires a better solution to ameliorate and alleviate the progression of the disease. CKD symptoms are diverse and mainly stem from organic waste products, called uremic retention solutes (URSs), that are normally cleared by the kidneys and accumulate in CKD patients. Among the URSs, protein-bound uremic toxins, such as indoxyl sulfate (IS) and p-cresyl sulfate (PCS), are derived from microbial metabolism and have deleterious effects on the cardiovascular system. Several treatments targeting URSs have been proposed, such as applying oral adsorbents to decrease their absorption and performing hemodialysis/kidney transplantation to increase their clearance. However, most of these treatments have limitations and disadvantages (Davenport, A. More frequent hemodialysis does not effectively clear protein-bound azotemic solutes derived from gut microbiome metabolism. *Kidney Int.* 2017, 91, 1008-1010).

Since the gut microbiota has a significant role in URSs production, numerous studies have revealed that the gut microbiota is associated with several pathological conditions, leading to accelerated CKD progression. Iatrogenic effects and alterations of physiological conditions, including pharmacological therapies, a slow intestinal transit time, impaired protein assimilation, and dietary restriction in CKD patients become the driving force to dysregulate the gut composition and expand the imbalance between symbionts and pathobionts that favors pathobiont overgrowth. However, the causality between the progression of CKD and gut dysbiosis is not completely understood.

Strategies based on microbiota-based therapeutic interventions, with the aim of modulating the gut microbiota and restoring the gut homeostasis by increasing the symbiotic bacteria or by absorptive removal or degradation of gut-derived precursors, could be considered as effective approaches to reduce uremic toxins. The efficacy of probiotics in decreasing uremic toxin production and improving renal functions has been investigated in in vitro models and in various animal and human CKD studies. However, to date, in vitro screening platforms with quality intervention trials examining this novel CKD therapy are still lacking.

SUMMARY OF THE INVENTION

Figure 1:
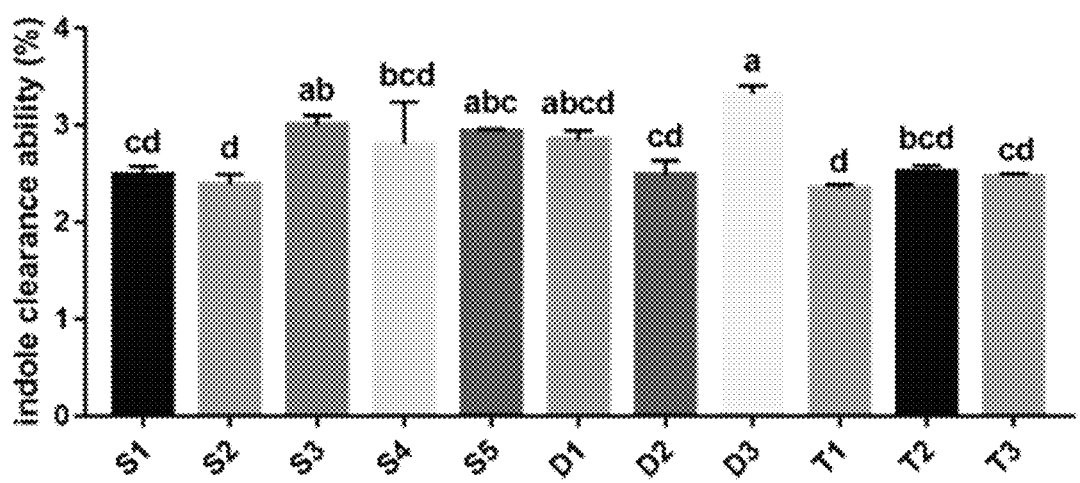
FIG. 1: Indole and p-cresol clearance ability of $10^9$ CFU/mL of test strains (S1: MFM 22; S2: MFM 30-2; S3: MFM 30-3; S4: MFM 18; S5: MFM 14-1; D1: MFM 22/18; D2: MFM 30-2/18; D3: MFM 30-3/18; T1: MFM 22/18/14-1; T2: MFM 30-2/18/14-1; T3: MFM 30-3/18-14-1) after 48 h of incubation in simulated intestinal juice. The results are presented as mean±SEM (n=3). Means in columns with different letters are significantly different (p<0.05).
Figure 1:
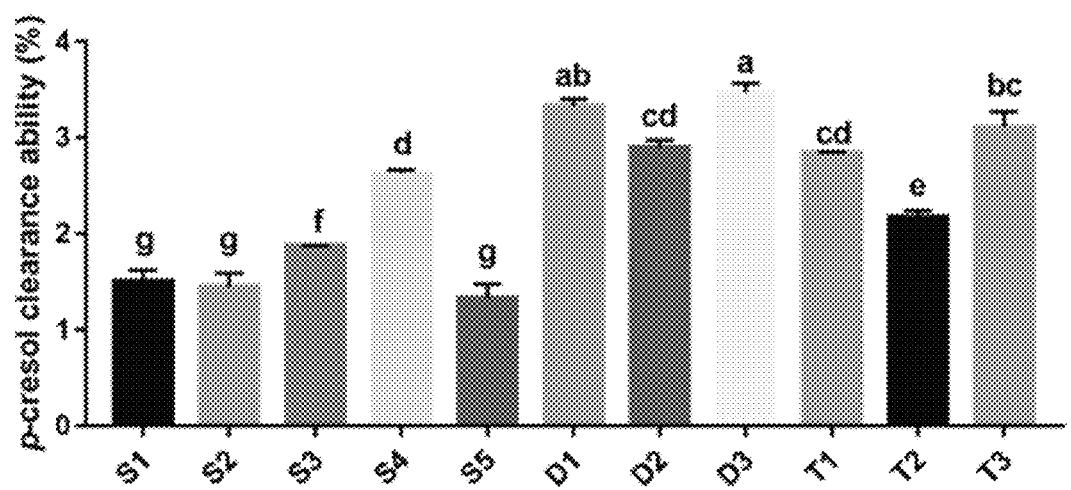

The present invention relates to an isolated bacterial strain of *Lactiplantibacillus plantarum* subsp. *plantarum* MFM 30-3 deposited under the DSMZ Accession No. DSM 34213. The present invention also relates to a probiotic composition comprising an isolated bacterial strain of *Lactiplantibacillus plantarum* subsp. *plantarum* MFM 30-3 deposited under the DSMZ Accession No. DSM 34213, and optionally, one or more additional probiotic organisms that enhance the probiotic activity of the *Lactiplantibacillus plantarum* subsp. *plantarum* MFM 30-3. The present invention further relates to a method for preventing or treating chronic kidney disease in a subject in need thereof comprising: administering to said subject a pharmaceutically effective amount of the probiotic composition comprising an isolated bacterial strain of *Lactiplantibacillus plantarum* subsp. *plantarum* MFM 30-3 deposited under the DSMZ Accession No. DSM 34213, and optionally, one or more additional probiotic organisms that enhance the probiotic activity of the *Lactiplantibacillus plantarum* subsp. *plantarum* MFM 30-3.

DETAILED DESCRIPTION OF THE INVENTION

In the present invention, a novel in vitro screening platform is developed to select potential probiotics with higher uremic toxin precursor reducing properties. An adenine-induced CKD mouse model is further utilized to elucidate the functional properties of the selected strains on CKD progression. The mechanisms underlying probiotic-prevented CKD progression are also evaluated through analysis of the microbiota and metabolome.

After an in vitro screening assay and simulated gastric and intestinal fluid tests, two strains, *Lactiplantibacillus plantarum* subsp. *plantarum* MFM 30-3 and *Lacticaseibacillus paracasei* subsp. *paracasei* MFM 18, are chosen for further characterization. A combination of the above two strains is selected and named lactic acid bacteria mix (Lm) for further studies. The results show that Lm significantly improved the kidney function by reducing kidney injury and fibrotic-related proteins. Furthermore, Lm decreases oxidative stress and proinflammatory reactions and elevates immune responses in the kidney. Importantly, Lm reverses gut dysbiosis and restores the abundance of commensal bacteria, especially short-chain fatty acid producers, leading to improved intestinal barrier integrity via modulation of microbial composition and metabolite production. Taken together, these findings provide evidence that Lm can be a preventive or even therapeutic approach against CKD.

The term "*Lactiplantibacillus plantarum* subsp. *plantarum*" is formerly known as "*Lactobacillus plantarum* subsp. *plantarum*" which has been officially reclassified from April 2020 according to Zheng J et al. (Zheng J, Wittouck S. et al., (2020) 'A taxonmonic note on the genus *Lactobacillus*: Description of 23 novel genera, emended description of the genus *Lactobacillus* Beijerinck 1901, and union of Lactobacillusceae and Leuconostocaceae'. *Int. J. Syst. Evol. Microbiol*, 70 (4): 2782-2858).

The term "*Lacticaseibacillus paracasei* subsp. *paracasei*" is formerly known as "*Lactobacillus paracasei* subsp. *paracasei*" which has also been officially reclassified from April 2020 according to Zheng J et al. (Zheng J, Wittouck S. et al., (2020) 'A taxonmonic note on the genus *Lactobacillus*: Description of 23 novel genera, emended description of the genus *Lactobacillus* Beijerinck 1901, and union of Lactobacillaceae and Leuconostocaceae'. *Int. J. Syst. Evol. Microbiol*, 70 (4): 2782-2858).

The term "probiotic" is intended to mean a microorganism (such as a bacterium or a yeast) having a beneficial effect on the general health of an animal or a human, or a beneficial effect on a specific health problem, disorder or disease, alleviating pain, symptoms or discomfort associated with those health problem, disorder or disease.

The expression "probiotic composition" is intended to mean a general product comprising at least one probiotic. It will be understood that this expression encompasses a variety of specific products, all presenting the characteristic of comprising at least one probiotic.

The term "CFU", or "colony forming unit", is a unit commonly used to estimate the concentration of microorganisms in a test sample. The number of visible colonies (CFU) present on an agar plate can be multiplied by the dilution factor to provide a CFU/ml result.

The term "intestinal barrier", also referred to as "intestinal mucosal barrier", refers to the property of the intestinal mucosa that ensures adequate containment of undesirable luminal contents within the intestine while preserving the ability to absorb nutrients. The separation it provides between the body and the gut prevents the uncontrolled translocation of luminal contents into the body. Its role in protecting the mucosal tissues and circulatory system from exposure to pro-inflammatory molecules, such as microorganisms, toxins, and antigens is vital for the maintenance of health and well-being.

The term "about" as used herein is intended to reflect a variation of 10% of the value it is attached to. For example, a concentration of "about 20%" is reflective of a concentration ranging from 18% to 22%. As another example, a quantity of "about $10^8$" is reflective of a range of $0.9 \times 10^8$ to $1.1 \times 10^8$.

Therefore, the present invention provides an isolated bacterial strain of *Lactiplantibacillus plantarum* subsp. *plantarum* MFM 30-3 deposited under the Budapest Treaty at Leibniz Institute DSMZ-German Collection of Microorganisms and Cell Cultures (Inhoffenstr. 7B, D-38124 Braunschweig, Germany) on Mar. 22, 2022 and has been given the DSMZ Accession No. DSM 34213 by the International Depositary Authority. The present invention also provides an isolated bacterial strain of *Lacticaseibacillus paracasei* subsp. *paracasei* MFM 18 deposited under the Budapest Treaty at Leibniz Institute DSMZ-German Collection of Microorganisms and Cell Cultures (Inhoffenstr. 7B, D-38124 Braunschweig, Germany) on Mar. 22, 2022 and has been given the DSMZ Accession No. DSM 34212 by the International Depositary Authority. The above biological materials were both subjected to the viability test and passed. The deposits were made for a term of at least thirty (30) years and at least five (5) years after the most recent request for the furnishing of a sample of the deposit was received by the depository. Both deposits will be irrevocably and without restrictions released upon the issuance of a patent. The certificates of deposits and viability statements of the *Lactiplantibacillus plantarum* subsp. *plantarum* MFM 30-3 and *Lacticaseibacillus paracasei* subsp. *paracasei* MFM 18 issued by DSMZ are submitted herewith. The present invention further provides a probiotic composition comprising an isolated bacterial strain of *Lactiplantibacillus plantarum* subsp. *plantarum* MFM 30-3 deposited under the DSMZ Accession No. DSM 34213, and optionally, one or more additional probiotic organisms that enhance the probiotic activity of the *Lactiplantibacillus plantarum* subsp. *plantarum* MFM 30-3. Also, a probiotic composition comprising an isolated bacterial strain of *Lacticaseibacillus paracasei* subsp. *paracasei* MFM 18 deposited under the DSMZ Accession No. DSM 34212, and optionally, one or more additional probiotic organisms that enhance the probiotic activity of the *Lacticaseibacillus paracasei* subsp. *paracasei* MFM 18 is provided.

In an embodiment, the probiotic composition of the present invention comprises an isolated bacterial strain of *Lactiplantibacillus plantarum* subsp. *plantarum* MFM 30-3 deposited under the DSMZ Accession No. DSM 34213, and an isolated bacterial strain of *Lacticaseibacillus paracasei* subsp. *paracasei* MFM 18 deposited under the DSMZ Accession No. DSM 34212. In another embodiment, the quantity ratio of MFM 30-3: MFM 18 in the probiotic composition of the present invention is between 2:1 and 1:2. In yet another embodiment, the quantity ratio of MFM 30-3: MFM 18 in the probiotic composition of the present invention is 1:1.

The probiotic composition of the present invention may be presented in solid, liquid or semi solid form and may be taken by routes selected from oral, rectal, or parenteral. The probiotic composition according to the invention may additionally comprises one or more suitable pharmaceutical/neutraceutical excipients/carriers to provide the same in a desired dosage form to achieve desired delivery. The suitable pharmaceutical/neutraceutical excipients may be selected from the group consisting of diluents, binders, polymers, fillers, vehicles, carriers, and disintegrants.

The probiotic composition of the present invention is suitable for use as a food, a food supplement, a nutraceutical or as a therapeutic.

The present invention still provides a method for preventing or treating chronic kidney disease in a subject in need thereof comprising: administering to said subject a pharmaceutically effective amount of a probiotic composition comprising an isolated bacterial strain of *Lactiplantibacillus plantarum* subsp. *plantarum* MFM 30-3 deposited under the DSMZ Accession No. DSM 34213, and optionally, one or more additional probiotic organisms that enhance the probiotic activity of the *Lactiplantibacillus plantarum* subsp. *plantarum* MFM 30-3. In an embodiment, the probiotic composition comprises an isolated bacterial strain of *Lactiplantibacillus plantarum* subsp. *plantarum* MFM 30-3 deposited under the DSMZ Accession No. DSM 34213, and an isolated bacterial strain of *Lacticaseibacillus paracasei* subsp. *paracasei* MFM 18 deposited under the DSMZ Accession No. DSM 34212. In an embodiment, the dosage of the probiotic composition is about $5\times10^5$ to about $5\times10^9$ CFU/ml. In another embodiment, the dosage of the probiotic composition is at least $5\times10^6$ CFU/ml. In yet another embodiment, the dosage of the probiotic composition is at least $5\times10^7$ CFU/ml. In an embodiment, the quantity ratio of MFM 30-3: MFM 18 in the probiotic composition used in the method is between 2:1 and 1:2. In another embodiment, the quantity ratio of MFM 30-3: MFM 18 in the probiotic composition used in the method is 1:1.

The present invention also provides a method for preventing or treating chronic kidney disease in a subject in need thereof comprising: administering to said subject a pharmaceutically effective amount of a probiotic composition comprising an isolated bacterial strain of *Lacticaseibacillus paracasei* subsp. *paracasei* MFM 18 deposited under the DSMZ Accession No. DSM 34212, and optionally, one or more additional probiotic organisms that enhance the probiotic activity of the *Lacticaseibacillus paracasei* subsp. *paracasei* MFM 18. In an embodiment, the probiotic composition comprises an isolated bacterial strain of *Lactiplantibacillus plantarum* subsp. *plantarum* MFM 30-3 deposited under the DSMZ Accession No. DSM 34213, and an isolated bacterial strain of *Lacticaseibacillus paracasei* subsp. *paracasei* MFM 18 deposited under the DSMZ Accession No. DSM 34212. In an embodiment, the dosage of the probiotic composition is about $5\times10^5$ to about $5\times10^9$ CFU/ml. In another embodiment, the dosage of the probiotic composition is at least $5\times10^6$ CFU/ml. In yet another embodiment, the dosage of the probiotic composition is at least $5\times10^7$ CFU/ml. In an embodiment, the quantity ratio of MFM 30-3: MFM 18 in the probiotic composition used in the method is between 2:1 and 1:2. In another embodiment, the quantity ratio of MFM 30-3: MFM 18 in the probiotic composition used in the method is 1:1.

In an embodiment, the method for preventing or treating chronic kidney disease of the present invention reduces the content of the indicative molecule selected from indole, p-cresol, indoxyl sulfate, or p-cresyl sulfate. In another embodiment, the method for preventing or treating chronic kidney disease of the present invention reverses gut dysbiosis and restores the abundance of commensal bacteria. In yet another embodiment, the method for preventing or treating chronic kidney disease of the present invention improves intestinal barrier integrity via modulation of microbial composition and metabolite production.

EXAMPLES

The examples below are non-limiting and are merely representative of various aspects and features of the present invention.

Example 1

Materials and Methods

Bacterial Strains

Lactic acid bacteria (LAB) strains were isolated from Mongolian fermented milk (MFM). For strain isolation, the process of Watanabe et al. (Watanabe, K.; Fujimoto, J.; Sasamoto, M.; Dugersuren, J.; Tumursuh, T.; Demberel, S. Diversity of lactic acid bacteria and yeasts in Airag and Tarag, traditional fermented milk products *World J. Microbiol. Biotechnol.* 2008, 24, 1313-1325) was adopted with slight modifications. Briefly, homogenized samples were subjected to serial 10-fold dilutions with saline and 0.1 mL aliquots were inoculated onto modified MRS agar plates supplemented with 2% lactose (Bioshop Canada Inc, Canada), 0.001% both of cycloheximide (Sigma-Aldrich), and sodium azide (Sigma-Aldrich) and incubated anaerobically at 30° C. for 3 days. The colonies were selected according to distinct morphologies (size, color, and shape). The isolates were then purified by streaking at least three times on the modified MRS agar plates. For strain discrimination of the isolates, Enterobacterial repetitive intergenic consensus polymerase chain reaction (ERIC-PCR) analysis was performed as previously described (Ventura, M.; Meylan, V.; Zink, R. Identification and tracing of *Bifidobacterium* species by use of enterobacterial repetitive intergenic consensus sequences. Appl. Environ. Microbiol. 2003, 69, 4296-4301). On the basis of the resulting ERIC-PCR profiles, one representative strain for each of the 40 groups were chosen and cultured for frozen storage and further analysis. Followed by the detailed strain typing of the 40 strains by the combination of ERIC-PCR and random amplified polymorphic DNA (RAPD)—PCR, the 20 strains were discriminated from 12 strains, which were assigned with branch numbers (as listed in Table 1). Before subsequent analysis, the isolates were cultured twice with 1% inoculum in modified MRS broth (2% lactose) at 30 or 37° C. for 24 or 48 h depending on different strains.

TABLE 1

Indole Clearance Ability of LAB Strains

| Strain | Indole clearance ability (%) after hrs of incubation | | | |
|---|---|---|---|---|
| | 0 | 24 | 48 | 72 |
| MFM 1 | 3.81 ± 0.43 | 4.57 ± 0.19 | 2.85 ± 1.03 | 6.57 ± 0.67 |
| MFM 2 | 2.28 ± 0.54 | 4.32 ± 0.33 | 4.02 ± 0.79 | 5.35 ± 0.98 |
| MFM 2-1 | 1.95 ± 0.27 | 4.15 ± 0.19 | 4.47 ± 1.33 | 5.30 ± 0.57 |
| MFM 2-2 | 3.81 ± 0.31 | 3.36 ± 0.25 | 4.55 ± 1.39 | 4.09 ± 0.82 |
| MFM 2-3 | 4.61 ± 0.56 | 4.37 ± 0.35 | 5.01 ± 0.51 | 4.65 ± 0.64 |
| MFM 3 | 4.48 ± 0.84 | 4.77 ± 0.88 | 5.35 ± 0.15 | 5.90 ± 0.51 |
| MFM 3-1 | 4.04 ± 0.49 | 4.46 ± 0.14 | 5.59 ± 0.82 | 6.04 ± 0.63 |
| MFM 3-2 | 4.04 ± 0.71 | 3.95 ± 0.54 | 4.94 ± 0.36 | 4.80 ± 1.32 |
| MFM 3-3 | 4.24 ± 0.27 | 4.01 ± 0.14 | 4.74 ± 0.55 | 5.01 ± 0.66 |
| MFM 4 | 2.86 ± 0.60 | 3.24 ± 0.51 | 5.14 ± 1.21 | 3.96 ± 0.12 |
| MFM 5 | 2.34 ± 0.38 | 4.01 ± 0.73 | 4.28 ± 0.57 | 2.67 ± 1.30 |
| MFM 6 | 2.02 ± 0.39 | 1.88 ± 0.60 | 4.22 ± 0.22 | 3.87 ± 1.29 |
| MFM 7 | 1.33 ± 0.35 | 2.25 ± 0.26 | 5.54 ± 1.90 | 4.23 ± 0.56 |
| MFM 8 | 3.90 ± 1.22 | 3.16 ± 0.76 | 6.28 ± 0.77 | 6.17 ± 0.41 |
| MFM 9 | 2.01 ± 0.36 | 4.79 ± 0.67 | 3.08 ± 0.72 | 2.02 ± 0.27 |
| MFM 10 | 2.75 ± 0.45 | 5.53 ± 0.23 | 4.95 ± 0.74 | 5.68 ± 0.96 |
| MFM 11 | 3.60 ± 0.19 | 5.75 ± 1.92 | 6.71 ± 0.31 | 6.72 ± 1.21 |
| MFM 12 | −4.97 ± 1.94 | 3.01 ± 0.43 | 5.55 ± 0.13 | 7.33 ± 0.47 |
| MFM 13 | 4.78 ± 0.16 | 4.79 ± 0.43 | 5.37 ± 0.49 | 5.53 ± 0.16 |
| MFM 13-1 | 2.86 ± 0.30 | 3.88 ± 0.50 | 3.92 ± 1.20 | 4.14 ± 1.48 |
| MFM 13-2 | 4.16 ± 0.54 | 4.70 ± 0.72 | 3.64 ± 0.62 | 3.83 ± 0.79 |
| MFM 14-1 | −4.46 ± 6.75 | 2.57 ± 0.72 | 5.87 ± 0.14 | 8.50 ± 1.96 |
| MFM 14-2 | −5.93 ± 2.71 | 2.73 ± 0.21 | 6.40 ± 2.30 | 6.59 ± 0.47 |
| MFM 15-1 | 3.86 ± 0.10 | 4.15 ± 0.54 | 2.54 ± 0.36 | 5.91 ± 0.20 |
| MFM 15-1-1 | 3.94 ± 0.09 | 4.85 ± 0.20 | 1.98 ± 0.49 | 6.20 ± 0.20 |
| MFM 15-1-2 | 3.30 ± 0.79 | 4.61 ± 0.90 | 6.06 ± 0.56 | 5.77 ± 0.57 |
| MFM 15-2 | 3.89 ± 0.20 | 5.00 ± 0.28 | 5.38 ± 1.05 | 6.22 ± 1.25 |
| MFM 16 | 4.32 ± 0.64 | 4.87 ± 0.98 | 4.55 ± 1.38 | 3.54 ± 2.17 |
| MFM 17 | 2.84 ± 0.37 | 6.25 ± 0.27 | 4.37 ± 0.65 | 5.40 ± 0.63 |
| MFM 18 | 4.82 ± 0.08 | 6.57 ± 0.09 | 9.22 ± 1.14 | 10.13 ± 0.72 |
| MFM 19 | 3.01 ± 0.58 | 3.25 ± 0.54 | 2.99 ± 0.86 | 2.76 ± 1.04 |
| MFM 19-1 | 3.59 ± 0.51 | 4.58 ± 0.07 | 4.79 ± 0.41 | 4.65 ± 0.43 |
| MFM 20 | 1.45 ± 0.43 | 6.57 ± 0.53 | 4.21 ± 0.89 | 5.39 ± 0.19 |
| MFM 21-1 | 6.10 ± 0.14 | 6.32 ± 0.52 | 6.12 ± 0.30 | 6.52 ± 1.20 |
| MFM 21-2 | 3.13 ± 0.44 | 4.44 ± 0.29 | 5.48 ± 0.90 | 5.83 ± 1.00 |
| MFM 22 | 5.12 ± 0.22 | 7.84 ± 0.43 | 9.09 ± 0.60 | 9.93 ± 0.92 |
| MFM 23 | 3.22 ± 0.48 | 7.54 ± 0.36 | 5.70 ± 0.31 | 6.10 ± 1.57 |
| MFM 23-1 | 2.37 ± 0.65 | 4.53 ± 1.87 | 6.57 ± 2.21 | 5.00 ± 0.92 |
| MFM 24 | 3.58 ± 0.42 | 4.18 ± 0.59 | 5.61 ± 0.20 | 5.18 ± 1.21 |
| MFM 25 | 3.14 ± 0.55 | 4.69 ± 0.57 | 2.69 ± 0.34 | 4.10 ± 0.87 |
| MFM 26-1 | 6.50 ± 0.33 | 6.18 ± 0.54 | 7.27 ± 0.53 | 7.28 ± 0.37 |
| MFM 26-2 | 2.20 ± 1.48 | 1.41 ± 1.43 | 3.85 ± 1.84 | 2.31 ± 0.56 |
| MFM 27 | 2.44 ± 0.30 | 7.50 ± 0.59 | 5.30 ± 0.44 | 5.55 ± 0.35 |
| MFM 28 | 2.46 ± 0.07 | 3.17 ± 0.11 | 3.53 ± 1.19 | 5.89 ± 3.80 |
| MFM 29 | 3.23 ± 0.23 | 4.46 ± 0.09 | 7.08 ± 0.71 | 7.30 ± 1.23 |
| MFM 30-1 | 1.75 ± 0.39 | 6.96 ± 0.21 | 4.04 ± 0.64 | 4.14 ± 0.71 |
| MFM 30-2 | 3.44 ± 0.56 | 8.23 ± 0.76 | 6.71 ± 0.81 | 6.88 ± 0.32 |
| MFM 30-3 | 3.46 ± 0.58 | 8.65 ± 1.30 | 10.30 ± 3.89 | 8.00 ± 0.35 |
| MFM 31 | 3.12 ± 0.91 | 8.01 ± 0.22 | 5.85 ± 0.28 | 5.00 ± 0.44 |
| MFM 32 | 4.68 ± 0.41 | 5.05 ± 0.73 | 2.25 ± 0.99 | 6.71 ± 1.30 |
| MFM 33 | 5.51 ± 0.80 | 7.16 ± 0.28 | 7.89 ± 0.46 | 7.05 ± 0.86 |
| MFM 34 | 4.20 ± 0.66 | 6.00 ± 0.36 | 5.65 ± 0.71 | 5.82 ± 1.53 |
| MFM 35-1 | 2.83 ± 0.29 | 4.29 ± 0.75 | 4.67 ± 0.62 | 5.25 ± 0.60 |
| MFM 35-2 | 1.90 ± 0.47 | 3.11 ± 0.41 | 3.82 ± 0.99 | 4.02 ± 0.60 |
| MFM 36 | 3.90 ± 0.72 | 6.10 ± 0.28 | 4.98 ± 1.06 | 4.89 ± 0.70 |
| MFM 37 | 4.96 ± 0.31 | 4.70 ± 0.45 | 1.20 ± 0.89 | 4.07 ± 0.86 |
| MFM 38 | 3.44 ± 0.34 | 4.33 ± 0.20 | 5.76 ± 0.18 | 6.73 ± 0.15 |
| MFM 39 | 4.18 ± 0.09 | 4.36 ± 0.11 | 1.47 ± 0.53 | 4.09 ± 0.58 |
| MFM 40 | 6.23 ± 0.14 | 6.20 ± 0.30 | 9.77 ± 3.93 | 7.27 ± 1.23 |

The results are presented as the mean ± SD (n = 3).
Bacterial number is $10^9$ to $10^{10}$ CFU per milliliter of simulated intestinal juice.

Uremic Toxin Precursor Clearance Ability of LAB Strains

Before test, the 60 isolates were cultured twice with 1% inoculum in modified MRS broth (2% lactose) at 30 or 37° C. for 24 or 48 h depending on different strains. All isolates reached the stationary phase with cell numbers ranging from $10^9$ to $10^{10}$ CFU/mL. Cells of test strains were centrifuged at 3300×g for 10 min. After discarding the supernatant, the cells were incubated in simulated intestinal juice (0.05 M $KH_2PO_4$, pH 7.25) with 200 ppm indole or 100 ppm p-cresol for 24-72 h. After incubation, the cells were centrifuged again, the supernatant was collected, and the concentrations of indole and p-cresol were determined. The potential strains with high clearance ability were selected. To choose the possible combination with the best clearance result, the selected strains were adjusted to $10^9$ CFU/mL with saline and performed the uremic toxin precursor clearance test, as described previously.

Identification of LAB

Genomic DNA of the LAB strains was extracted. The 16S rRNA gene was amplified with the primers 8F and 15R (Watanabe, K.; Fujimoto, J.; Sasamoto, M.; Dugersuren, J.; Tumursuh, T.; Demberel, S. Diversity of lactic acid bacteria and yeasts in Airag and Tarag, traditional fermented milk products of Mongolia. *World J. Microbiol. Biotechnol.* 2008, 24, 1313-1325). Phenylalanyl-tRNA synthase (pheS) and RNA polymerase A subunit (rpoA) genes were amplified with the primers pheS-21-F and pheS-23-R and rpoA-21-F and rpoA-23-R, respectively (Naser, S. M.; Thompson, F. L.; Hoste, B.; Gevers, D.; Dawyndt, P.; Vancanneyt, M.; Swings, J. Application of multilocus sequence analysis (MLSA) for rapid identification of *Enterococcus* species based on rpoA and pheS genes. *Microbiology* 2005, 151, 2141-2150). Full-length sequencing of the 16S rRNA gene was performed with the primers 350F, 520R, and 930F (Miyake, T.; Watanabe, K.; Watanabe, T.; Oyaizu, H. Phylogenetic analysis of the genus *Bifidobacterium* and related genera based on 16S rDNA sequences. *Microbiol. Immunol.* 1998, 42, 661-667), and partial sequencing of the pheS and rpoA genes was performed with the previously described primers. All sequence analyses were carried out at Genomics BioSci & Tech Co., Ltd. (New Taipei, Taiwan). The sequences were assembled by using Chromas version 2.23 (Technelysium Pty. Ltd., QLD, Australia), GENETYX version 5.1, and GENETYX ATSQ version 1.03 (Software Development Co., Tokyo, Japan). Phylogenetic trees were constructed by the neighbor-joining method by using Clustal X software version 2.1 (Thompson, J.; Gibson, T. J.; Plewniak, F.; Jeanmougin, F.; Higgins, D. G. The CLUSTAL_X windows interface: flexible strategies for multiple sequence alignment aided by quality analysis tools. *Nucleic Acids Res.* 1997, 25, 4876-4882). The statistical reliability of the trees was evaluated by bootstrap analysis of 1000 replicates by using MEGA7 v7.0.14 software according to Kimura's two-parameter model as a substitution model (Kumar, S.; Stecher, G.; Tamura, K. MEGA7: Molecular evolutionary genetics analysis version 7.0 for bigger datasets. *Mol. Biol. Evol.* 2016, 33, 1870-1874).

Gastrointestinal Tolerance

LAB isolated strains were cultured twice with 1% inoculum in modified MRS broth (2% lactose) at 30 or 37° C. for 24 h depending on different strains. All isolates reached the stationary phase with cell numbers ranging from $10^9$ to $10^{10}$ CFU/mL. Cells of test strains were centrifuged at 3300×g for 10 min and washed twice with saline. After discarding the supernatant, cells were completely dispersed in simulated gastric juice (3.6 mM $CaCl_2$), 1.5 mM $MgCl_2$, 49 mM NaCl, 12 mM KCl, and 6.4 mM $KH_2PO_4$, pH 2.0) containing 1600 U/mL pepsin (Sigma-Aldrich) and incubated at 37° C. with 120 rpm shaking for 1 h. Then, the cells were dispersed in simulated intestinal juice (0.1 M $NaHCO_3$, pH 8.0) containing 4.4 g/L porcine bile and 1 g/L pancreatin (Sigma-Aldrich) for 2 h. Surviving bacteria were counted in modified MRS agar aerobically incubated at 30 and 37° C. for 2 days (Yonekura, L.; Sun, H.; Soukoulis, C.; Fisk, I. Microencapsulation of *Lactobacillus acidophilus* NCIMB 701748 in matrices containing soluble fibre by spray drying: Technological characterization, storage stability and survival after in vitro digestion. *J. Funct. Foods* 2014, 6, 205-214).

Adenine-Induced CKD Animal Model

Male C57BL/6 mice (5 weeks old) were purchased from the National Laboratory Animal Center (Taipei, Taiwan) and housed in a specific pathogen-free (SPF) facility in the National Taiwan University Animal Resource Center with a 12 h light/dark cycle and free access to sterilized AIN93G pellets (Research Diets, Inc., New Brunswick, NJ, USA) and water. At 7 weeks of age, the mice were randomly divided into four groups [control, CKD, low dosage (LD), and high dosage (HD)]. The LD and HD groups were orally gavaged with 200 μL of a cell suspension equal to the low dosage [$10^7$ colony forming units (CFUs)/mice/day] and high dosage ($10^9$ CFUs/mice/day) of mixed lactic acid strains for 6 weeks, respectively. At the third week, all groups except for the control group were fed an AIN93G diet supplemented with 0.2% adenine (Research Diets) to induce CKD for 18 days and then returned to their original feed. At the end of the animal study, the mice were euthanized, and blood, organs, feces, and the colonic content were collected for further analysis. All of the animal experiments were approved by the Institutional Animal Care and Use Committee of National Taiwan University (IACUC approval no: NTU-107-EL-00053).

Biochemical Measurements

The assays for blood urea nitrogen (BUN) and creatinine (CRE) in serum were analyzed by an automated clinical chemistry analyzer (Fujifilm Corporation, Tokyo, Japan).

Indole and p-Cresol Analyses

In vitro, the concentrations of indole and p-cresol in the clearance ability test were measured using a high-performance liquid chromatography (HPLC) system (Jasco International Co. Ltd., Tokyo, Japan) and a Reprosil 100 C18 column (250×4.6 mm; 5 μm particle size; Dr. Maisch GmbH, Ammerbuch-Entringen, Germany) with an injection volume of 20 μL and a 1.0 mL/min flow rate. For analysis of the indole concentration, the mobile phase consisted of methanol and ultrapure water (65:35), and the wavelength was set at 254 nm. For analysis of the p-cresol concentration, the mobile phase consisted of methanol, ACN, and ultrapure water (15:26.3:58.7), and the wavelength was set to 210 nm. In vivo, due to the limited amounts of colonic contents and low concentrations of both precursors in colonic samples, a higher sensitivity and efficiency approach was adapted from Liu et al. (Liu, Y.; Li, J.; Yu, J.; Wang, Y.; Lu, J.; Shang, E. X.; Zhu, Z.; Guo, J.; Duan, J. Disorder of gut amino acids metabolism during CKD progression is related with gut microbiota dysbiosis and metagenome change. *J. Pharm. Biomed. Anal.* 2018, 149, 425-435). The colonic contents were homogenized in PBS (FastPrep-24 5G Instrument, MP Biomedicals, Irvine, CA, USA) and centrifuged at 16,100×g for 10 min at 4° C., and the supernatant was mixed with ACN (1:3, v/v). Analytes were measured using a HPLC system (Jasco International Co. Ltd., Tokyo, Japan) and a Reprosil 100 C18 column (250×4.6 mm; 5 μm particle size; Dr. Maisch GmbH, Ammerbuch-Entringen, Germany). Mobile phase A was 200 mM ammonium formate (pH 4.5), and mobile phase B was 100% ACN. The analytical conditions were isocratic at 48% B, and indole and p-cresol were eluted at 10.3 and 6.7 min, respectively. The injection volume was 20 µL, the flow rate was 1 mL/min, the autosampler tray temperature was 4° C., and the fluorescence detection settings for indole were $\lambda_{ex}$ 270 nm/$\lambda_{em}$ 340 nm and for p-cresol were $\lambda_{ex}$ 260 nm/$\lambda_{em}$ 300 nm.

Uremic Toxin Analysis

Serum was mixed with ACN (1:3, v/v), vortexed for 30 s, and then centrifuged at 9,300×g for 5 min at room temperature. Serum uremic toxin was measured using an HPLC system and a Reprosil 100 C18 column. Mobile phase A was 50 mM ammonium formate (pH 4.5), and mobile phase B was 100% ACN. The optimized conditions of the eluting gradient were as follows: 5-40% B (0-13.0 min), 40% B (13.0-16.0 min), and 5% B (16.0-22.0 min). The injection volume was 20 µL, the flow rate was 1 ml/min, and the autosampler tray temperature was 4° C. Indoxyl sulfate and p-cresyl sulfate were eluted at 11.0 and 12.6 min, respectively. The fluorescence detection settings for indoxyl sulfate were $\lambda_{ex}$ 300 nm/$\lambda_{em}$ 390 nm and for p-cresyl sulfate were $\lambda_{ex}$ 260 nm/$\lambda_{em}$ 283 nm (Pretorius, C. J.; McWhinney, B. C.; Sipinkoski, B.; Johnson, L. A.; Rossi, M.; Campbell, K. L.; Ungerer, J. P. J. Reference ranges and biological variation of free and total serum indoxyl- and p-cresyl sulphate measured with a rapid UPLC fluorescence detection method. Clin. Chim. Acta 2013, 419, 122-126).

Short-Chain Fatty Acid Analysis

The concentrations of fecal short-chain fatty acids (SCFAs) were measured as previously described with slight modifications (Torii, T.; Kanemitsu, K.; Wada, T.; Itoh, S.; Kinugawa, K.; Hagiwara, A. Measurement of short-chain fatty acids in human faeces using high-performance liquid chromatography: specimen stability. *Ann. Clin. Biochem.* 2010, 47, 447-452). After a series of procedures, the obtained fatty acids were dissolved in 200 µL of methanol. The concentration of SCFAs was measured using a HPLC system with a Reprosil 100 C18 column. The mobile phase consisted of ACN, methanol, and ultrapure water (30:16:54), and the pH was adjusted to 4.5 with 0.1% TFA (Sigma-Aldrich). The injection volume was 30 µL, the flow rate was 1.1 mL/min, the column temperature was 50° C., and the wavelength was set at 400 nm.

Kidney Antioxidant Enzyme Activity Analysis

The levels of glutathione (GSH), superoxide dismutase (SOD), catalase, and glutathione peroxidase (GPx) in the kidney were determined using a commercial kit (Cayman Chemical Co., Ann Arbor, MI, USA) according to the manufacturer's instructions.

Kidney Cytokine Analysis

The tumor necrosis factor (TNF)-α, interleukin (IL)-6, and IL-10 levels in plasma were measured using ELISA kits (R&D system, Minneapolis, MN, USA) according to the manufacturer's instructions.

Intestinal Permeability

Fluorescein isothiocyanate (FITC)—dextran (FD4) (Sigma-Aldrich) was dissolved in PBS (60 mg/mL), and mice were orally gavaged with 200 µL of FITC-dextran 4 h before blood collection. The serum was diluted 1:9 in PBS, and the fluorescence of FITC-dextran was determined using a fluorometer with settings of $\lambda_{ex}$ 485 nm/$\lambda_{em}$ 528 nm (BioTek, Winooski, VT, USA). Intestinal permeability was presented as the concentration of serum FITC-dextran (Woting, A.; Blaut, M. Small intestinal permeability and gut-transit time determined with low and high molecular weight fluorescein isothiocyanate-dextrans in C3H mice. Nutrients 2018, 10, 685).

Western Blot Analysis

Kidney lysates were separated by SDS-PAGE, transferred onto PVDF membranes (Merck Millipore Ltd., Burlington, MA, USA), and blotted at 4° C. overnight with primary antibodies against transforming growth factor (TGF)-β, fibronectin, collagen 1, myeloperoxidase (MPO), Toll-like receptor 4 (TLR4), and beta actin at a 1:1000 dilution, and at room temperature for 1 h with an horseradish peroxidase-conjugated goat anti-rabbit IgG antibody at a 1:10,000 dilution (all from Abcam, Cambridge UK) as the secondary antibody. The membrane was incubated with Western Lightning ECL Pro (PerkinElmer, Inc., Waltham, MA, USA) and detected using a ChemiDoc Imaging System (Bio-Rad Laboratories, Inc., Hercules, CA, USA).

16S rRNA Gene Amplicon Sequencing

DNA was extracted from colonic contents. The V3-V4 regions of the 16S rRNA gene were amplified by the universal primers 341F (5'-CCTACGGGAGGCAGCAG-3') (SEQ ID NO: 1) and 806R (5'-GGAC-TACCAGGGTATCTAAT-3') (SEQ ID NO: 2) with barcodes and sequenced using the MiSeq™ System (a paired-end DNA sequencing platform, Illumina Inc. San Diego, CA). Taxonomic annotation of the representative sequence for each operational taxonomic unit (OTU) was performed using the Ribosomal Database Project (RDP) classifier v2.2 against the Silva v.132 database. Alpha diversity (observed OTUs, Chao1, and Shannon) and beta diversity (principal component analysis, PCA) were analyzed using QIIME v1.7.0 and R v2.15.3 software. The linear discriminant analysis (LDA) effect size (LEfSe) algorithm was used for biomarker discovery to identify differential enrichment of abundant taxa between groups. For functional analysis, functional abundances from 16S rRNA sequencing data were analyzed for the prediction of functional genes with Phylogenetic Investigation of Communities by Reconstruction of Unobserved States (PICRUSt) v1.1.1 by using the Kyoto Encyclopedia of Genes and Genomes (KEGG) database of reference genomes (Langille, M. G. I.; Zaneveld, J.; Caporaso, J. G.; McDonald, D.; Knights, D.; Reyes, J. A.; Clemente, J. C.; Burkepile, D. E.; Vega Thurber, R. L.; Knight, R.; Beiko, R. G.; Huttenhower, C. Predictive functional profiling of microbial communities using 16S rRNA marker gene sequences. *Nat. Biotechnol.* 2013, 31, 814-821).

Statistical Analysis

For in vitro studies, data were compared using one-way ANOVA with Duncan's test as a post hoc test. For in vivo studies, unpaired t-tests and nonparametric Mann-Whitney U tests were performed for all the phenotypic and next-generation sequencing (NGS) data. A P value of <0.05 was considered statistically significant. Correlation analyses were performed by Spearman's correlation analysis. All statistical analyses were performed by SPSS Statistics 23.0 (IBM, New York, NY, USA), SAS v9.4 (SAS Institute Inc., Cary, NC, USA), and GraphPad Prism 7.00 software (San Diego, CA, USA).

Results

Two Lactic Acid Bacteria Strains with the Highest Clearance Ability for Uremic Toxin Precursors Were Selected.

To select potential uremic toxin-reducing probiotics, first, a novel screening platform was established by adding indole or p-cresol to simulated intestinal juice (pH 7.25) and inoculating it with isolates from Mongolian fermented milk. The 60 isolates were isolated from five Mongolian fermented milk products (Airag, Tarag, and their mixture) and selected because of their distinct genotyping profiles based on enterobacterial repetitive intergenic consensus polymerase chain reaction (ERIC-PCR) analysis (data not shown). Thirteen of 60 isolates (MFM 12, 14-1, 18, 22, 23, 26-1, 27, 29, 30-2, 30-3, 31, 33, and 40) were selected for further identification due to their higher indole clearance abilities (Table 1). The identification results from the analysis of 16S rRNA and housekeeping gene sequences indicated that the 13 isolates belonged to three lactic acid bacteria species: *Lactiplantibacillus plantarum* (six isolates), *Companilactobacillus crustorum* (six isolates), and *Lacticaseibacillus paracasei* (one isolate). To further select potential strains among the 13 strains, both indole and p-cresol clearance ability as well as the tolerance of simulated gastric and intestinal fluid tests were also determined. Three strains of *L. plantarum* (MFM 22, 30-2, and 30-3), one strain of *C. crustorum* (MFM 14-1), and one strain of *L. paracasei* (MFM 18) were selected (Table 2).

Pretreatment with Lm Prevented the Symptoms of Adenine-Induced Renal Injury in Mice.

Figure 2A:
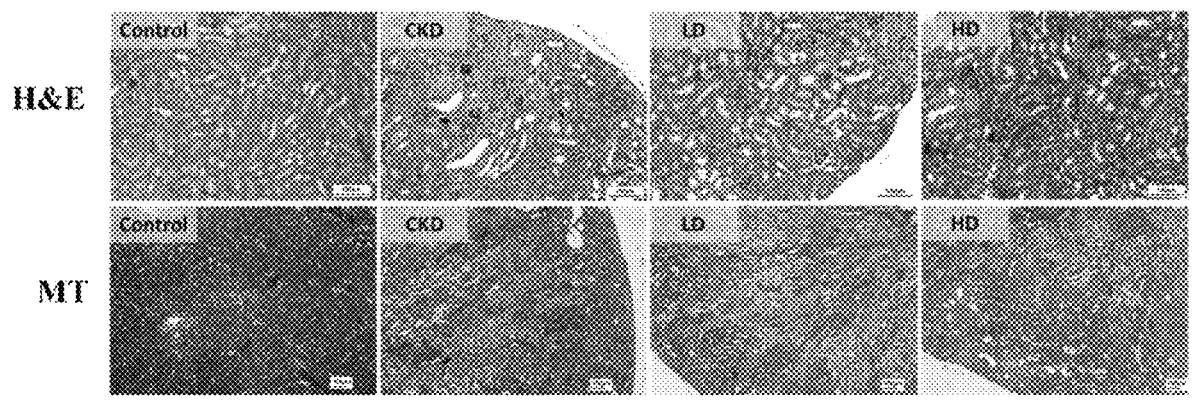
FIG. 2A: Representative images of H&E- and MT-stained kidney sections. Scale bar=100 μm. The kidney injury score and quantitative analysis of the interstitial fibrosis area are determined based on the H&E and MT results, respectively. The results are presented as mean±SEM (n=9-11). The symbols indicate a significant difference compared with the control (*p<0.05) and CKD groups (#p<0.05).
Figure 2A:
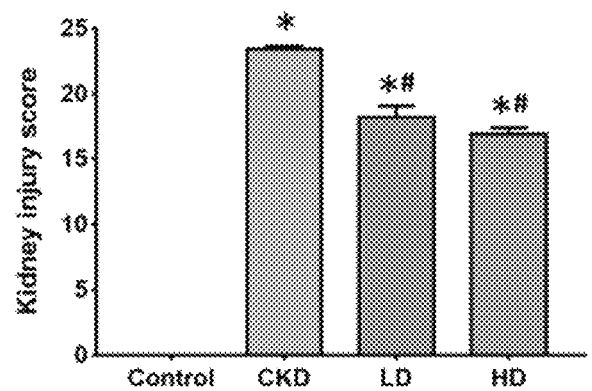
Figure 2A:
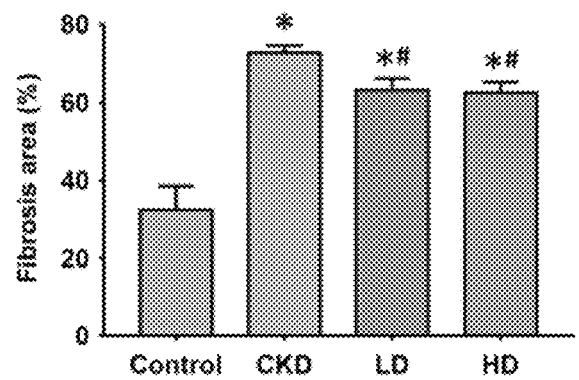
Figure 2B:
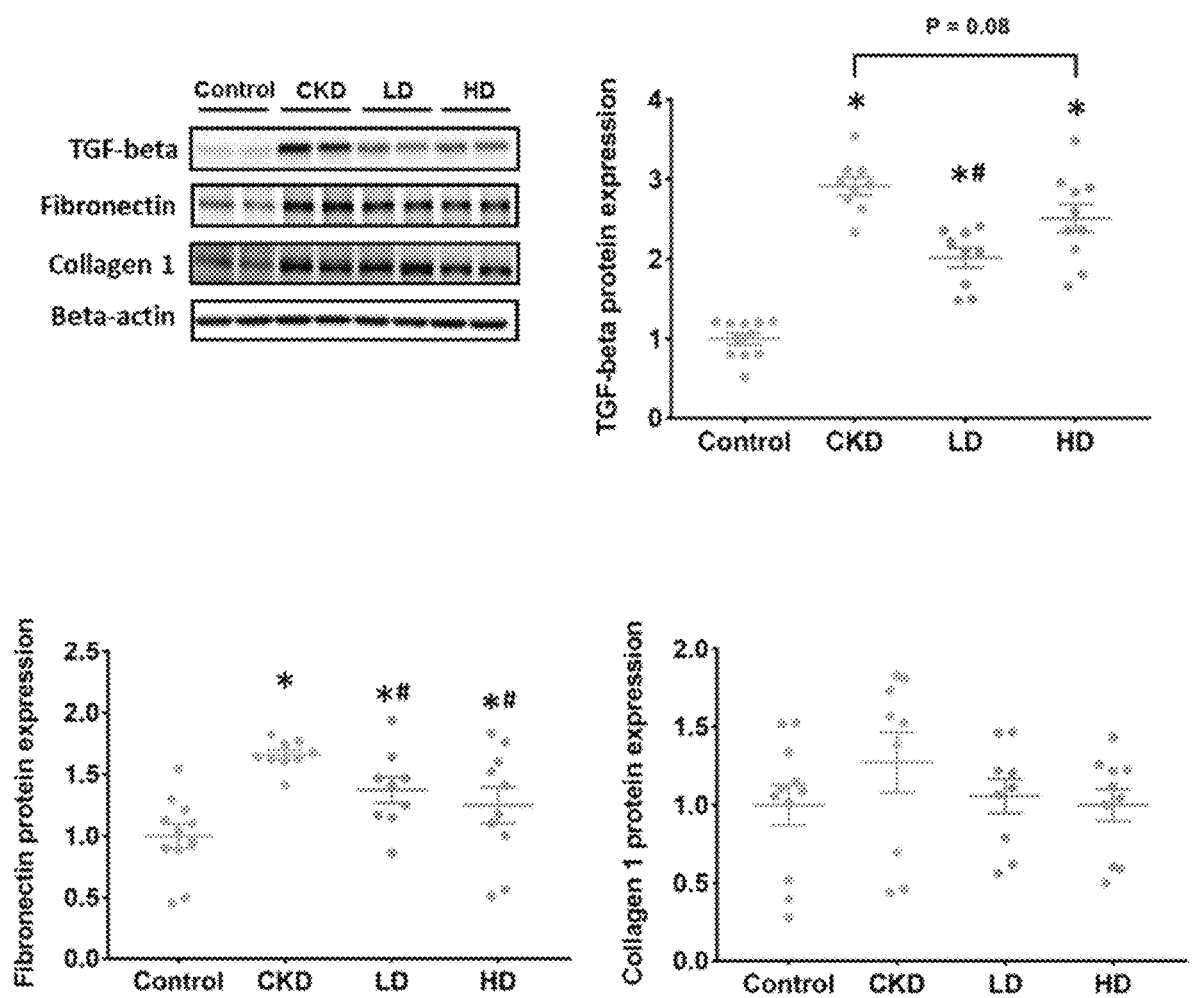
FIG. 2B: Western blot analysis of kidney fibrosis-related proteins are normalized to the beta-actin levels. The results are presented as mean±SEM (n=9-11). The symbols indicate a significant difference compared with the control (*p<0.05) and CKD groups (#p<0.05).
Figure 2C:
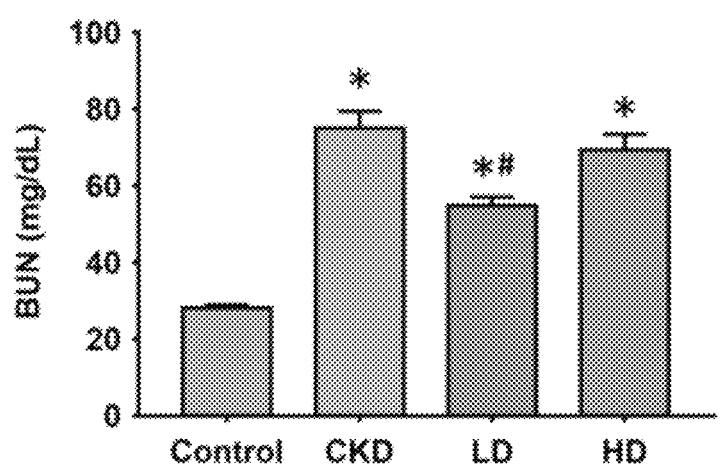
FIG. 2C: BUN and CRE analyses. The results are presented as mean±SEM (n=9-11). The symbols indicate a significant difference compared with the control (*p<0.05) and CKD groups (#p<0.05).
Figure 2C:
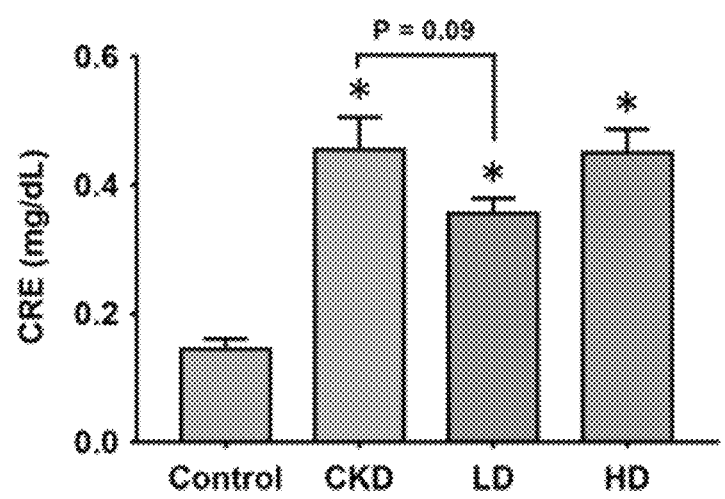

In vivo, after 18 days of 0.2% adenine administration, classic kidney lesions, including inflammation and fibrosis in the renal interstitium, atrophy, degeneration, necrosis, regeneration, and hyaline cast in the renal tubule, crystal deposition in the cortical surface, and dilation of Bowen's capsule in the renal corpuscle, were observed in CKD mice, with significantly increased kidney injury scores and fibrosis areas compared with the control group ($p<0.05$) (FIG. 2A). These findings were further confirmed by the activation of the potent fibrogenic factor TGFβ and the fibrosis markers fibronectin and collagen 1 ($p<0.05$) (FIG. 2B). BUN and CRE in serum, which are indicators of renal function, were also elevated significantly ($p<0.05$) (FIG. 2C). However, Lm intervention (LD and HD) prevented damage to the kidney structure by reducing the level of atrophy, degeneration, hyaline cast, dilation of Bowman's capsule, and crystal

TABLE 2

Characteristic Properties of MFM Isolates

| Taxonomic attribution | Strain | Gastrointestinal tolerance abilities[a] (Reduction of surviving cells represented as Log CFU/mL) | Clearance ability (%)[b] | |
|---|---|---|---|---|
| | | | Indole | p-cresol |
| Lactiplantibacillus plantarum | MFM 22 | $6.66 \pm 0.25^{a}$ | $9.01 \pm 0.40^{ab}$ | $6.24 \pm 0.36^{a}$ |
| | MFM 26-1 | $5.82 \pm 0.40^{bc}$ | $7.26 \pm 0.38^{c}$ | $4.39 \pm 0.22^{bc}$ |
| | MFM 30-2 | $5.29 \pm 0.26^{cd}$ | $9.70 \pm 0.36^{a}$ | $4.82 \pm 0.33^{b}$ |
| | MFM 30-3 | $6.10 \pm 0.28^{ab}$ | $9.03 \pm 0.58^{ab}$ | $5.88 \pm 0.26^{a}$ |
| | MFM 33 | $5.37 \pm 0.45^{cd}$ | $8.24 \pm 1.41^{bc}$ | $3.97 \pm 0.46^{c}$ |
| | MFM 40 | $4.88 \pm 0.34^{d}$ | $8.73 \pm 0.76^{ab}$ | $4.26 \pm 0.39^{bc}$ |
| Companilactobacillus crustorum | MFM 12 | $7.87 \pm 1.49$ | $6.94 \pm 0.50$ | $3.64 \pm 0.50$ |
| | MFM 14-1 | $7.27 \pm 0.93$ | $6.61 \pm 0.72$ | $2.78 \pm 0.63$ |
| | MFM 23 | $8.88 \pm 0.74$ | $7.09 \pm 0.14$ | $3.15 \pm 0.56$ |
| | MFM 27 | $8.56 \pm 1.35$ | $7.07 \pm 0.31$ | $3.07 \pm 0.29$ |
| | MFM 29 | $8.89 \pm 0.78$ | $7.30 \pm 0.16$ | $3.56 \pm 0.33$ |
| | MFM 31 | $8.10 \pm 1.62$ | $7.57 \pm 0.92$ | $2.51 \pm 1.13$ |
| Lacticaseibacillus paracasei | MFM 18 | $7.85 \pm 0.30$ | $9.42 \pm 0.86$ | $4.31 \pm 0.22$ |

[a]Gastrointestinal tolerance abilities of MFM isolates after in vitro digestion in simulated gastric juice and simulated intestinal juice.
[b]Indole and p-cresol clearance ability of MFM isolates after a 48 h incubation in simulated intestinal juice. The results are presented as the mean ± SD (n = 3). Means in columns with different superscript letters among the same species are significantly different ($p < 0.05$).

Additionally, the above selected strains were mixed to compare their clearance ability with that of the selected single strains (Table 3). The results showed that the probiotics mixed with MFM 30-3 and MFM 18 (D3) demonstrated the highest clearance ability of indole ($3.32\pm0.15\%$) and p-cresol ($3.47\pm0.16\%$) compared with the other groups. A combination of two strains (MFM 30-3 and MFM 18) was selected and named lactic acid bacteria mix (Lm) for further animal studies (FIG. 1).

TABLE 3

Various Combinations of Bacterial Strains

| Single strain | Double strains | Triple strains |
|---|---|---|
| S1: MFM 22 | D1: MFM 22/18 | T1: MFM 22/18/14-1 |
| S2: MFM 30-2 | D2: MFM 30-2/18 | T2: MFM 30-2/18/14-1 |
| S3: MFM 30-3 | D3: MFM 30-3/18 | T3: MFM 30-3/18/14-1 |
| S4: MFM 18 | Ratio: 1:1 | Ratio: 1:1:1 |
| S5: MFM 14-1 | Bacterial content: | Bacterial content: |
| Bacterial content: | $10^9$ CFU/mL | $10^9$ CFU/mL |
| $10^9$ CFU/mL | | | deposition, with a significantly lower kidney injury score and fibrosis area than their CKD counterparts ($p<0.05$) (FIG. 2A). Lm treatment significantly improved tubulointerstitial fibrosis by markedly reducing the expression of TGFβ ($p<0.1$) and its downstream activation of fibronectin (FIG. 2B). Downregulation of serum BUN and CRE was also observed in the LD group ($p<0.1$), suggesting a preventive effect of CKD progression by Lm (FIG. 2C).

Elevated Oxidative Stress and Immunosuppression in CKD Mice Were Partially Restored by Lm Treatment.

Figure 3A:
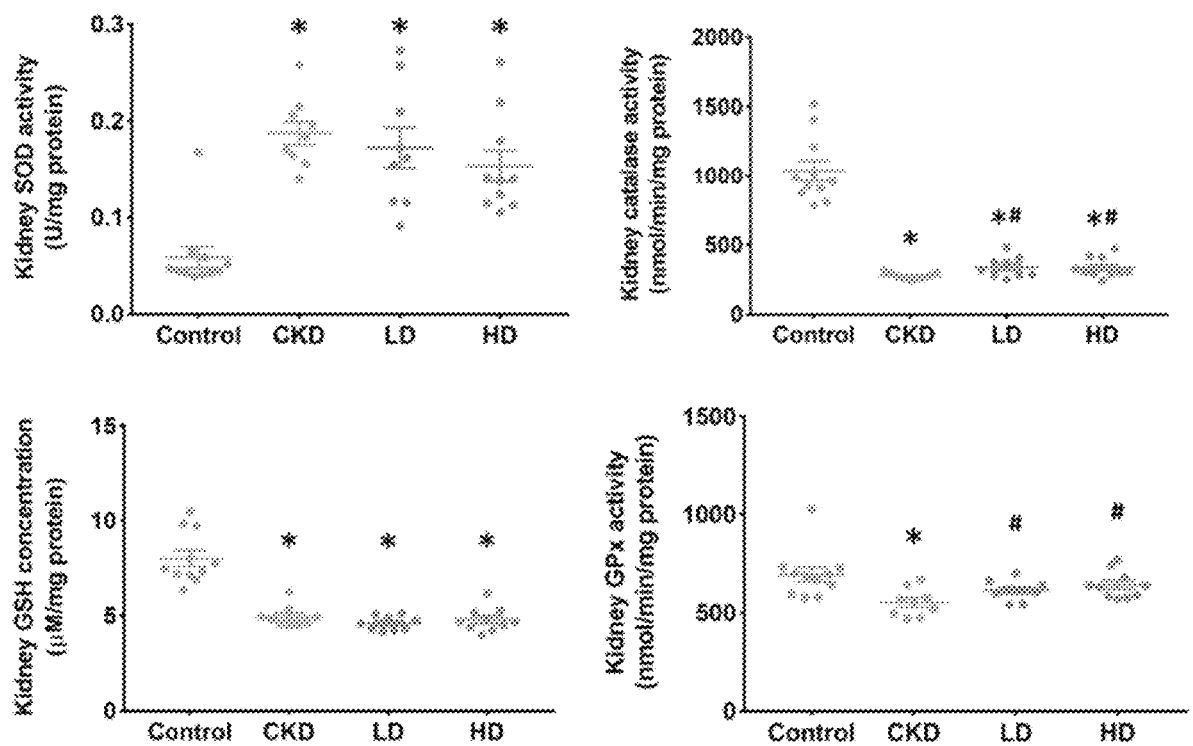
FIG. 3A: Activity of antioxidative protein. The results are presented as mean±SEM (n=9-11). The symbols indicate a significant difference compared with the control (*p<0.05) and CKD groups (#p<0.05).
Figure 3B:
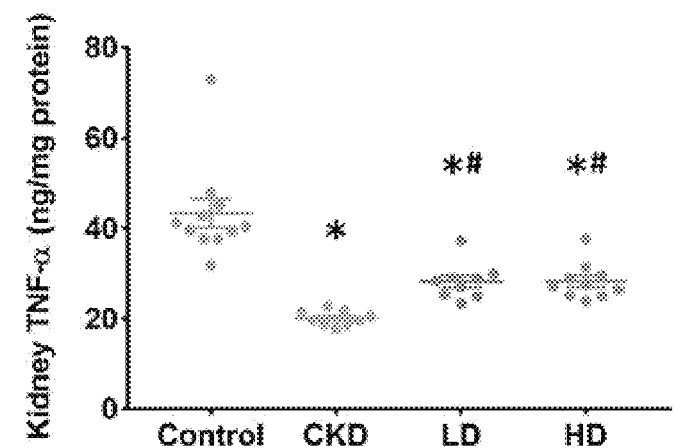
FIG. 3B: Concentration of cytokines. The results are presented as mean±SEM (n=9-11). The symbols indicate a significant difference compared with the control (*p<0.05) and CKD groups (#p<0.05).
Figure 3B:
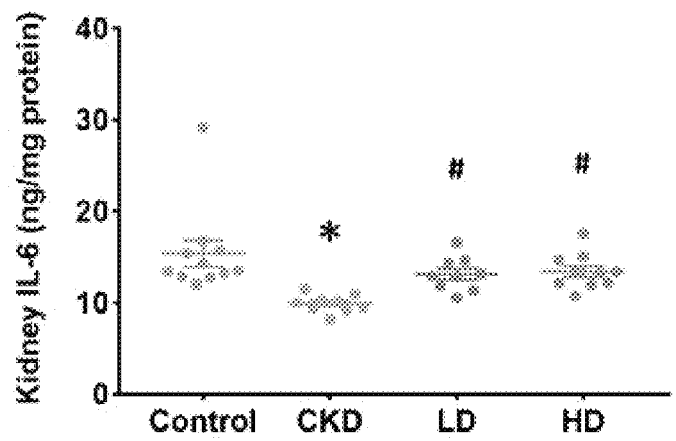
Figure 3B:
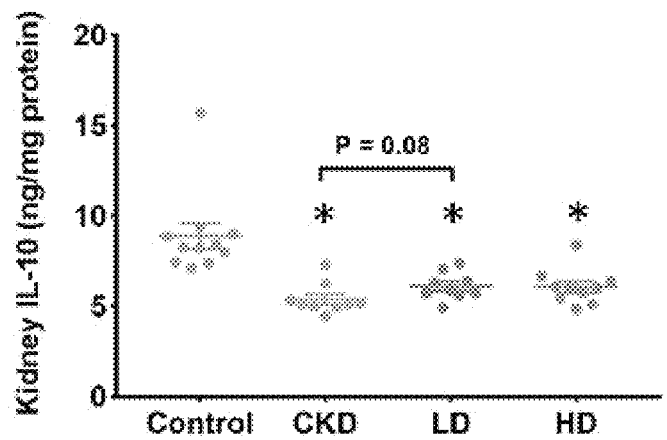
Figure 3C:
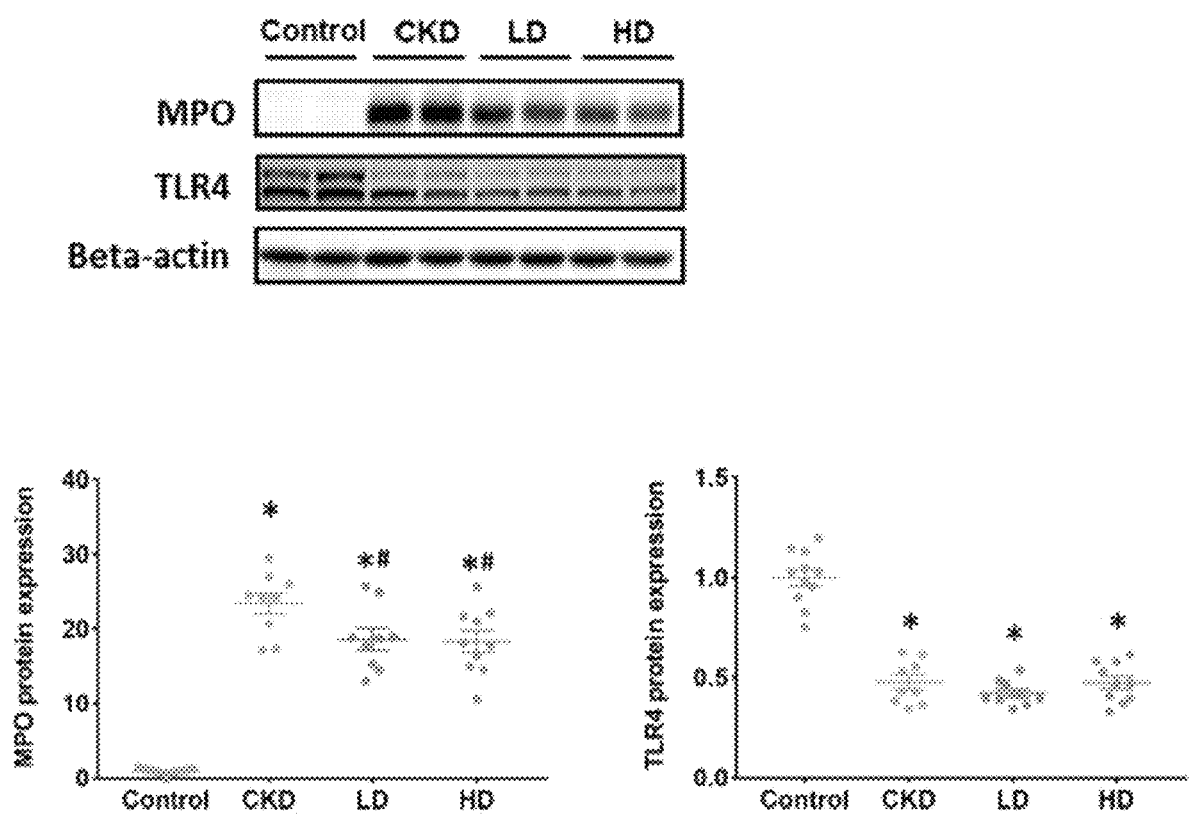
FIG. 3C: Western blot analysis of kidney oxidative stress and inflammatory response indicators are normalized to the beta-actin level. The results are presented as mean±SEM (n=9-11). The symbols indicate a significant difference compared with the control (*p<0.05) and CKD groups (#p<0.05).

The possible mechanisms involved in the preventive effect of Lm treatment on CKD were then investigated. Systematic oxidative stress and inflammation as well as immune dysregulation were well recognized as critical exacerbating factors in the progression of CKD. Thus, antioxidant enzymes and inflammation-related cytokines in the kidney were studied. The results indicated that the CKD group had elevated oxidative stress; significantly lower GSH, catalase, and GPx levels; and higher SOD levels than the control group. However, the levels of catalase and GPx were significantly restored ($p<0.05$) by Lm intervention in CKD mice (FIG. 3A). It was also found that the levels of proinflammatory cytokines (TNF-α and IL-6), the anti-inflammatory cytokine IL-10, and the protein expression of TLR4 in the kidneys of CKD mice were significantly lower than those in the kidneys of control mice (p<0.05) (FIGS. 3B-3C), suggesting immunosuppression in CKD mice. The expression of MPO, an enzyme that has a positive correlation with the inflammatory state, was significantly increased in CKD mice compared with control mice (p<0.05) (FIG. 3C). In contrast, Lm supplementation restored the levels of TNF-α and IL-6 and decreased the expression of MPO (*p<0.05) (FIGS. 3B-3C).

Lm Intervention Reduced the Levels of Uremic Toxins and Their Precursors.

Figure 4:
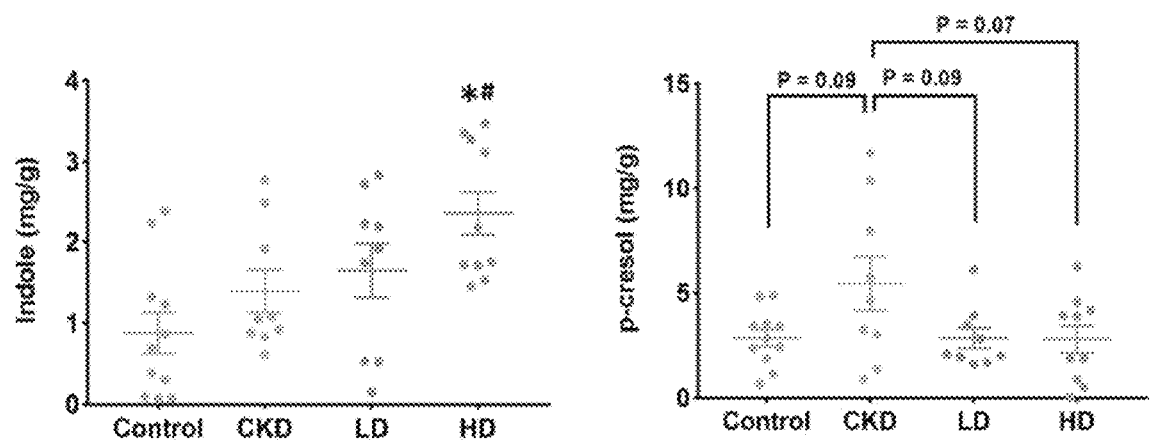
FIG. 4: Colonic uremic toxin precursors and serum uremic toxins. (A) Concentration of uremic toxin precursors in the colonic content. (B) Concentration of uremic toxins in serum. The results are presented as mean±SEM (n=9-11). The symbols indicate a significant difference compared with the control (*p<0.05) and CKD groups (#p<0.05).
Figure 4:
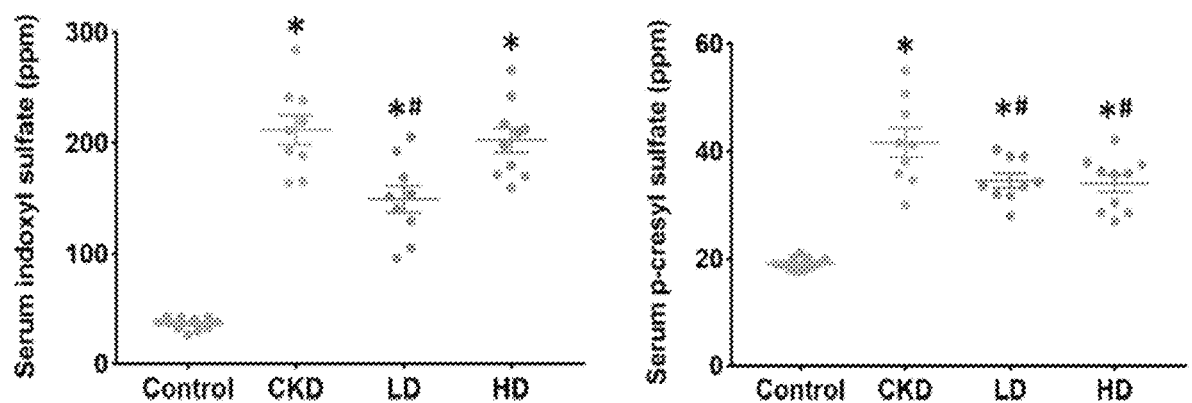

The indole and p-cresol levels were first determined. The results indicated that colonic indole and p-cresol were increased in CKD mice, resulting in significantly increased serial IS and PCS (p<0.05) compared with control mice. The low-dose Lm (Lm-LD) intervention showed a trend of reduced p-cresol (p<0.1) and further significantly downregulated the levels of serum IS and PCS (p<0.05). The high-dose Lm (Lm-HD) intervention also showed a trend of reduced p-cresol (p<0.1) and further significantly downregulated the levels of serum PCS (p<0.05), suggesting that Lm administration has positive impacts on the improvement of CKD progression (FIG. 4) by modulating the uremic toxin precursor.

Lm Intervention Improves Intestinal Barrier Integrity.

Figure 5A:
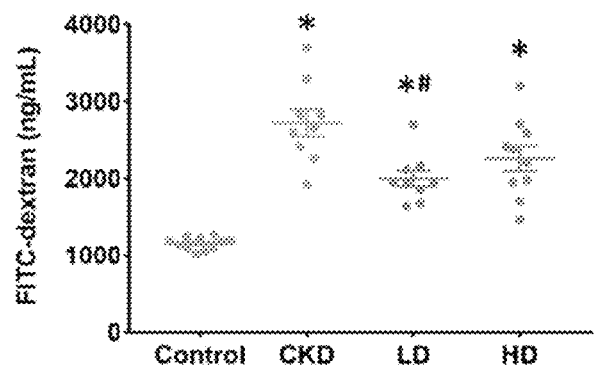
FIG. 5A: Serum concentration of FITC-dextran. The results are presented as mean±SEM (n=9-11). The symbols indicate a significant difference compared with the control (*p<0.05) and CKD groups (#p<0.05).
Figure 5B:
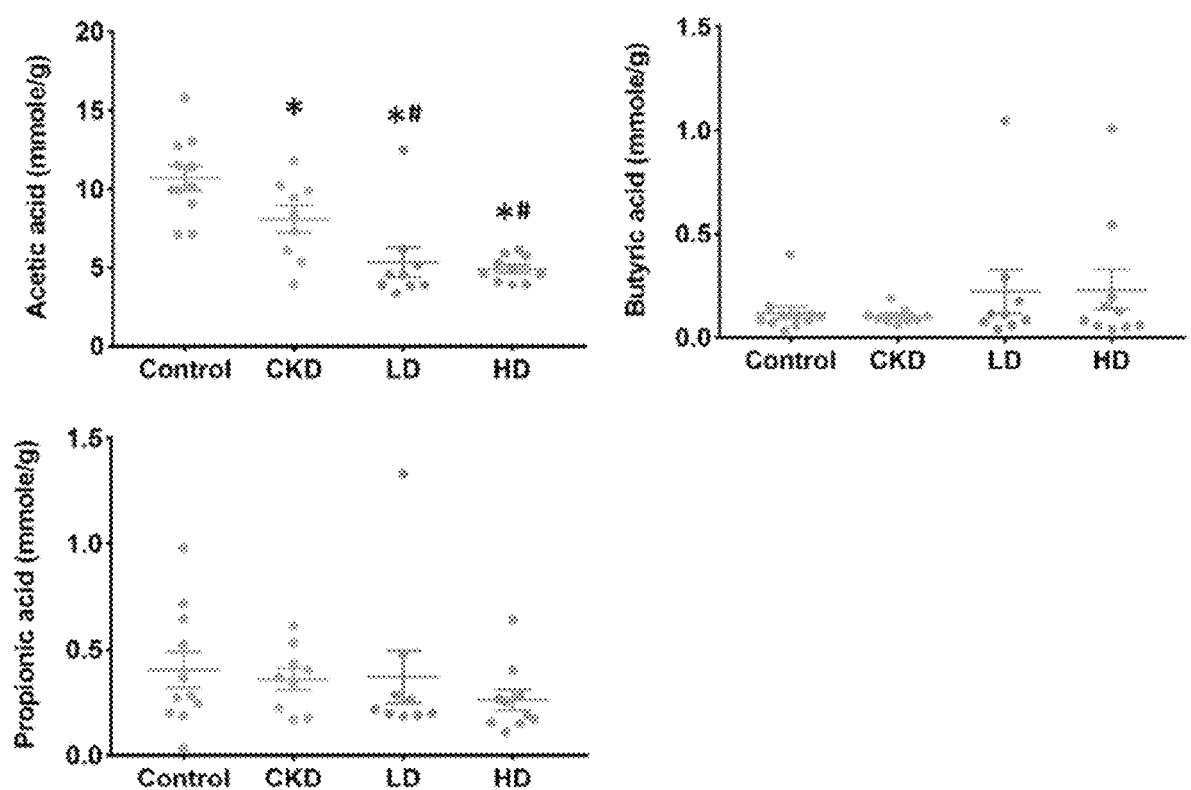
FIG. 5B: Fecal concentration of SCFA. The results are presented as mean±SEM (n=9-11). The symbols indicate a significant difference compared with the control (*p<0.05) and CKD groups (#p<0.05).

For intestinal barrier integrity, a significant increase in fluorescence intensity in the serum of the CKD group was observed (p<0.05) after oral administration of FITC-dextran. Treatment with Lm-LD significantly reduced gut permeability (p<0.05) in CKD mice (FIG. 5A). The SCFA results indicated that although probiotic treatment had no effects on the elevation of acetic acid and propionic acid, Lm intervention showed a trend of upregulating the level of butyric acid (FIG. 5B).

Lm Intervention Significantly Recovered Gut Dysbiosis and Changed Enriched Taxa in the Colon of CKD Mice.

Figure 6A:
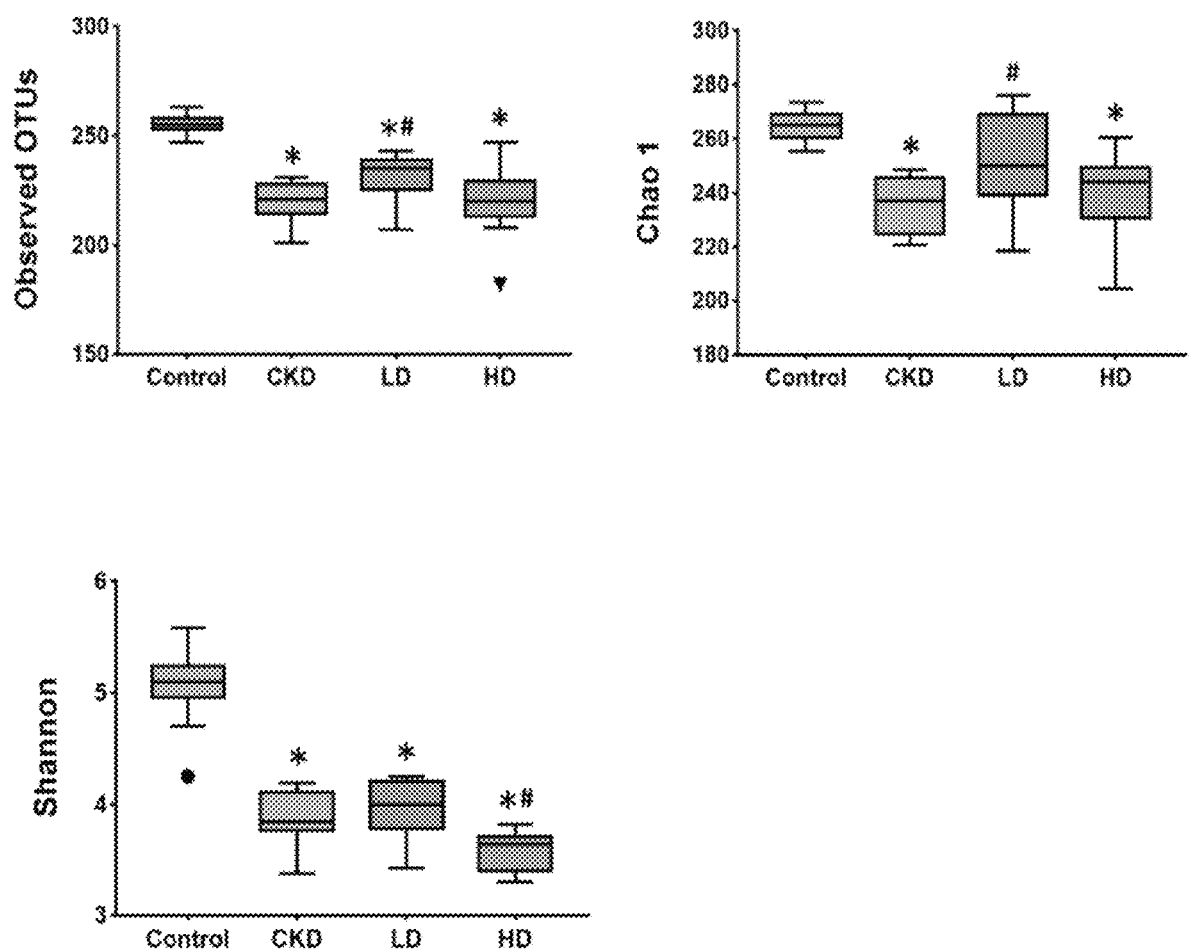
FIG. 6A: Comparison of alpha diversity between the colonic microbiome of each group (n=9-11). The symbols indicate a significant difference compared with control (*p<0.05) and CKD mice (#p<0.05).
Figure 6B:
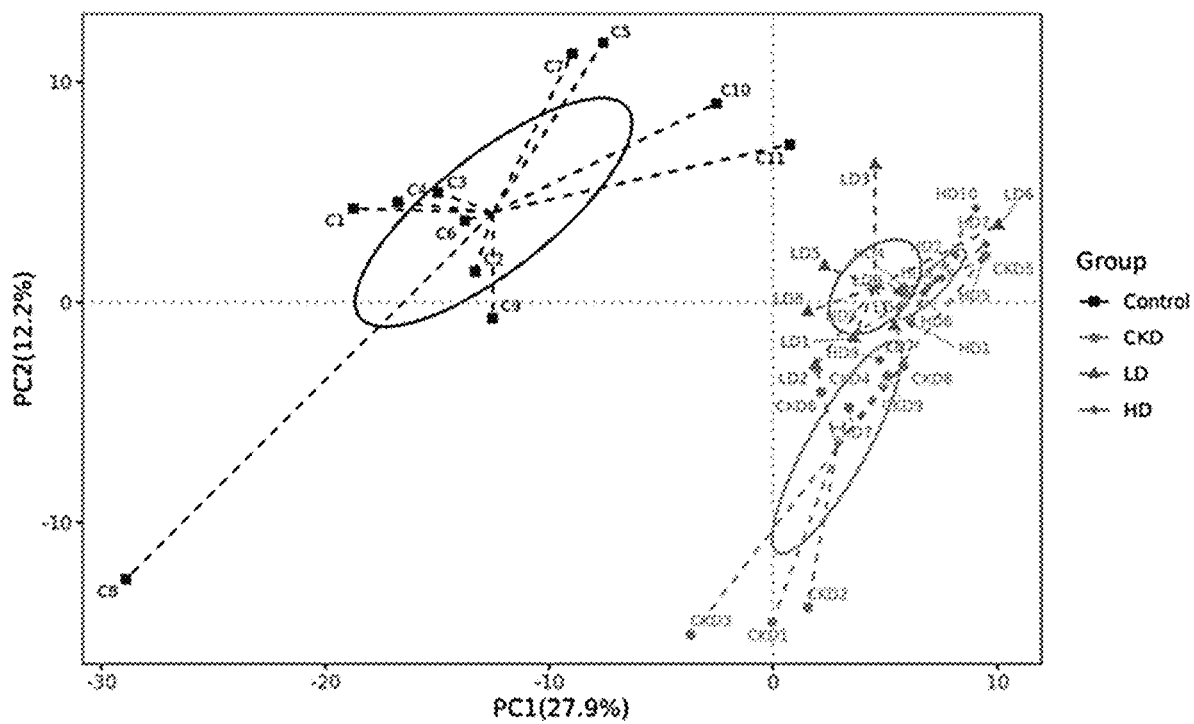
FIG. 6B: PCA plot based on the relative abundance of bacterial taxa of individual mice.

The gut microbial composition in the colon was further analyzed to clarify the role of Lm in the modulation of the intestinal microbiota. The alpha diversity indices (Observed_otus, Chao 1 and Shannon) were decreased significantly in the CKD group, suggesting the transition from a more even and diverse community to a more dominant and identical composition in the intestinal environment, which was driven by CKD induction. Administration of Lm-LD led to a significant restoration of richness and abundance in CKD mice (FIG. 6A). Beta diversity, calculated by PCA, was utilized to examine microbial composition differences between the tested groups. The PCA plot showed that PCA1 and PCA2 explained 27.9 and 12.2% of the variation in gut microbiota composition, respectively. Notably, obvious intergroup distances tended to form distinct clusters among each group, illustrating the dissimilar gut microbiota harbored in the colon (FIG. 6B). These findings suggested that the dysbiotic state due to CKD induction could be modulated through Lm intervention toward an intermediate configuration between control and CKD mice.

Figure 7A:
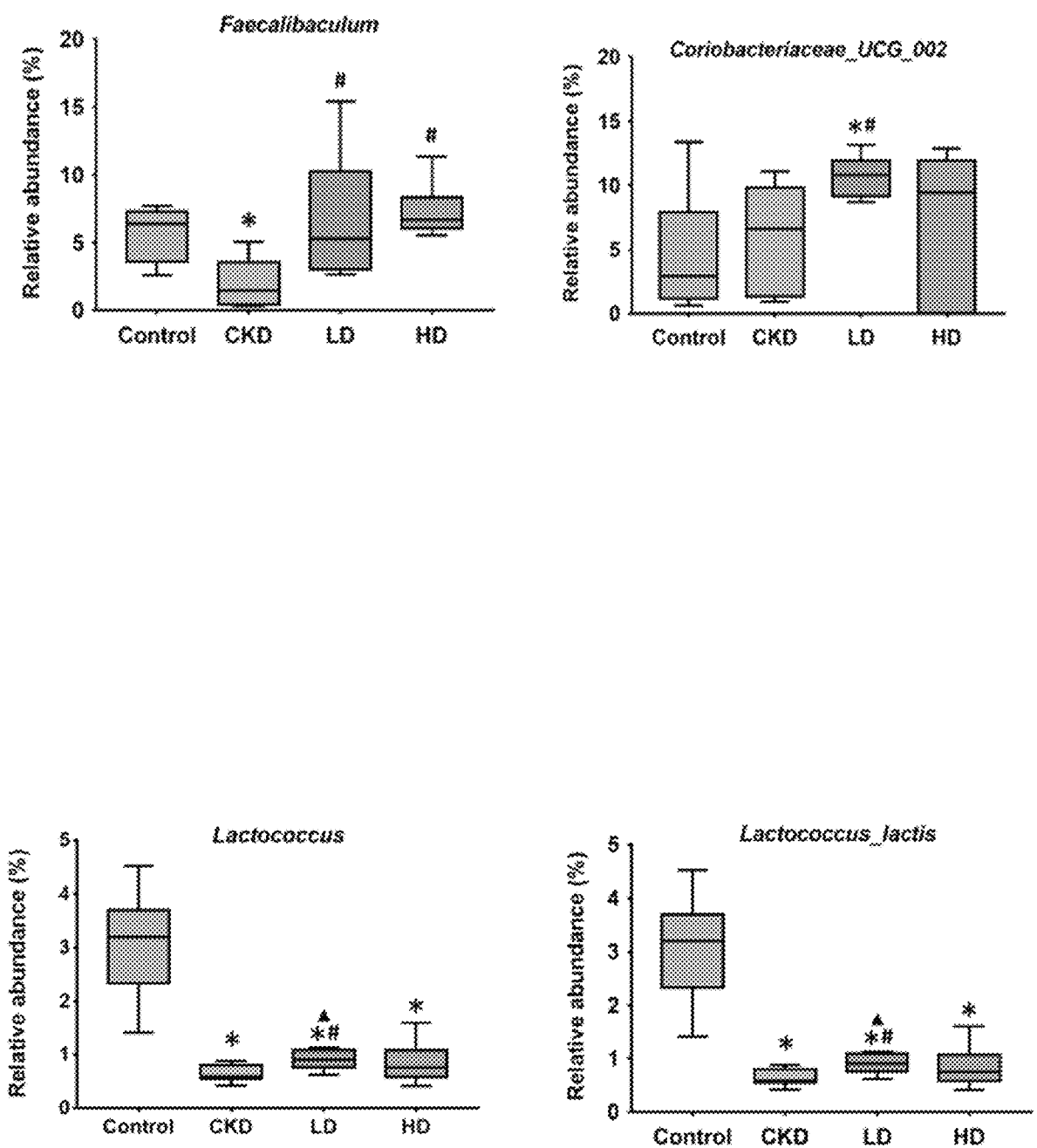
FIG. 7A: Relative abundance of bacterial genera or species enriched in LD mice compared to CKD mice (n=9-11).
Figure 7B:
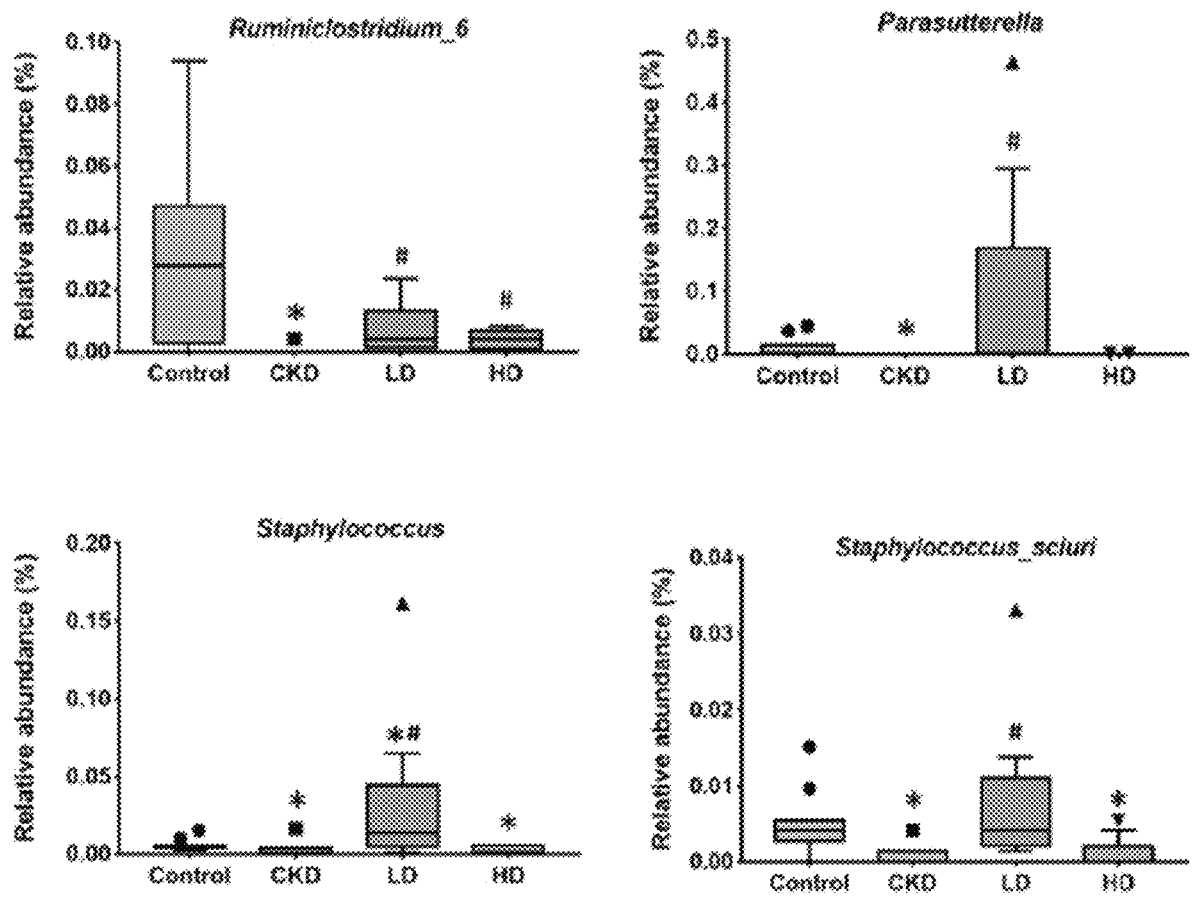
FIG. 7B: Relative abundance of bacterial genera or species enriched in LD mice compared to CKD mice (n=9-11). The symbols indicate a significant difference compared with the control (*p<0.05) and CKD groups (#p<0.05).
Figure 7C:
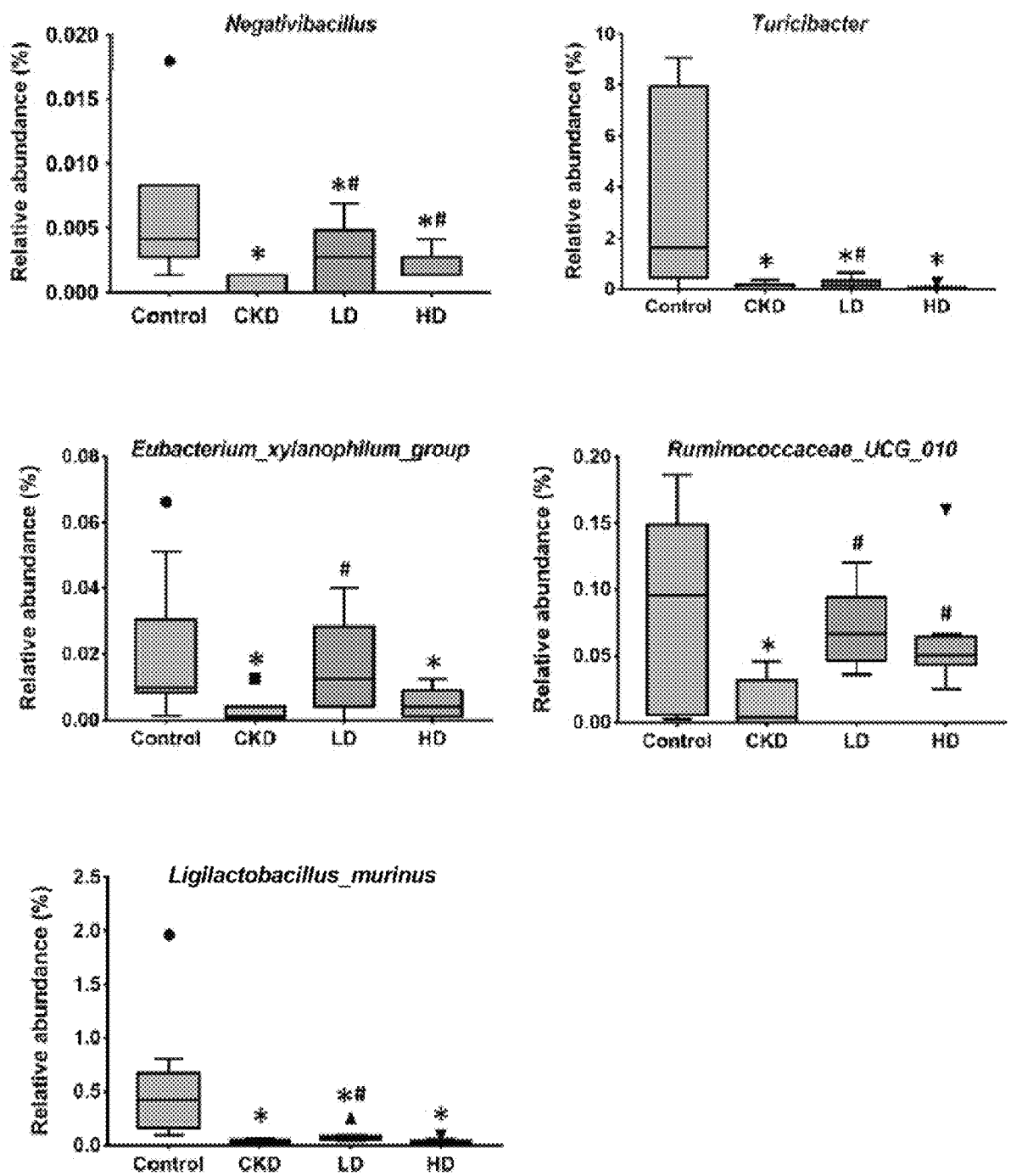
FIG. 7C: Relative abundance of bacterial genera or species enriched in LD mice compared to CKD mice (n=9-11). The symbols indicate a significant difference compared with the control (*p<0.05) and CKD groups (#p<0.05).

Since the data indicated that the Lm-LD group demonstrated greater efficiency than the Lm-HD group in alleviating CKD progression and improving dysbiosis, taxonomic differences between the CKD and Lm-LD mice were further identified. Administering Lm-LD specifically influenced 10 genera (Faecalibaculum, Coriobacteriaceae UCG 002, Lactococcus, Negativibacillus, Turicibacter, Ruminiclostridium 6, Parasutterella, Eubacterium xylanophilum group, Ruminococcaceae UCG 010 and Staphylococcus) and 3 species (Lactococcus lactis, Staphylococcus sciuri, and Ligilactobacillus murinus) which were commensal bacteria especially short chain fatty acid (SCFA) producers in the gut, indicating that the diminishment of these specific bacteria caused by CKD induction could be restored by Lm supplementation (FIGS. 7A-7C).

One skilled in the art readily appreciates that the present invention is well adapted to carry out the objects and obtain the ends and advantages mentioned, as well as those inherent therein. The bacterial strain, probiotic composition comprising the bacterial strain, and uses thereof are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations, which are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method for treating chronic kidney disease in a subject in need thereof comprising: administering to said subject a pharmaceutically effective amount of a composition comprising an isolated bacterial strain of *Lactiplantibacillus plantarum* subsp. *plantarum* MFM 30-3 deposited under the DSMZ Accession No. DSM 34213 and optionally, an isolated bacterial strain of *Lacticaseibacillus paracasei* subsp. *paracasei* MFM 18 deposited under the DSMZ Accession No. DSM 34212 that enhances the probiotic activity of the *Lactiplantibacillus plantarum* subsp. *plantarum* MFM 30-3, wherein the subject is taking penicillin.

2. The method of claim 1, which reduces the content of an indicative molecule selected from indole, p-cresol, indoxyl sulfate, or p-cresyl sulfate.

3. The method of claim 1, which reverses gut dysbiosis and restores the abundance of commensal bacteria.

4. The method of claim 1, which improves intestinal barrier integrity.

* * * * *

SEQUENCE LISTING

```
Sequence total quantity: 2
SEQ ID NO: 1            moltype = DNA  length = 17
FEATURE                 Location/Qualifiers
source                  1..17
                        mol_type = other DNA
                        organism = synthetic construct
misc_feature            1..17
                        note = PCR_primers_fwd_seq
```

```
SEQUENCE: 1
cctacgggag gcagcag                                                                          17

SEQ ID NO: 2              moltype = DNA  length = 20
FEATURE                   Location/Qualifiers
source                    1..20
                          mol_type = other DNA
                          organism = synthetic construct
misc_feature              1..20
                          note = PCR_primers_rev_seq
SEQUENCE: 2
ggactaccag ggtatctaat                                                                       20
```